United States Patent [19]

Bizière et al.

[11] Patent Number: 4,624,952
[45] Date of Patent: Nov. 25, 1986

[54] PYRIDAZINE AND PYRIMIDINE COMPOUNDS ACTIVE ON THE CENTRAL NERVOUS SYSTEM AS SEDATIVES OR ANTICONVULSANTS

[75] Inventors: Kathleen Bizière, Clapiers; Jean-Pierre Chambon, Montarnaud; André Hallot, St. Gely du Fesc, all of France

[73] Assignee: Sanofi, Paris, France

[21] Appl. No.: 570,832

[22] Filed: Jan. 16, 1984

[30] Foreign Application Priority Data

Jan. 21, 1983 [FR] France ................. 83 00954

[51] Int. Cl.$^4$ ................. C07D 401/04; C07D 237/20; A61K 31/445; A61K 31/50
[52] U.S. Cl. ................. 514/252; 544/224; 544/230; 544/238; 544/332; 514/247; 514/275
[58] Field of Search ............ 544/331, 332, 224, 230, 544/238; 514/252, 247, 275

[56] References Cited

U.S. PATENT DOCUMENTS 4,169,158  9/1979  Laborit ................. 514/247
4,302,455  11/1981  Huff et al. ............. 544/336

FOREIGN PATENT DOCUMENTS 72299  2/1983  European Pat. Off. ......... 544/224
73161  3/1983  European Pat. Off. ......... 544/224

Primary Examiner—Donald G. Daus
Assistant Examiner—William A. Teoli, Jr.
Attorney, Agent, or Firm—Stevens, Davis, Miller & Mosher

[57] ABSTRACT

The present invention relates to the compounds of formula

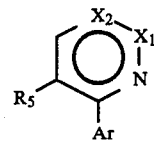

in which $X_1$ represents N or

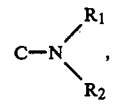

$X_2$ represents N or

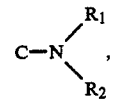

provided that $X_1$ and $X_2$ are different from each other; $R_1$ and $R_2$ being —$(CH_2)_n$OH wherein n is 1 to 4 or

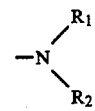

represents a saturated heterocycle with 5 or 6 groupings containing one nitrogen atom as heteroatom, substituted in 3 or 4 position for example by $(CH_2)_m OR_6$ where $R_6$ is H or an acyl radical or an amido radical; to a process for preparing said compounds; and to the drugs containing said compounds active in particular on the central nervous system.

23 Claims, No Drawings

PYRIDAZINE AND PYRIMIDINE COMPOUNDS ACTIVE ON THE CENTRAL NERVOUS SYSTEM AS SEDATIVES OR ANTICONVULSANTS

The present invention relates to novel heterocyclic compounds presenting interesting therapeutic properties on the central nervous system.

The compounds according to the invention are described by the general formula:

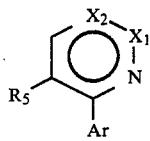

in which:

$X_1$ represents N or the

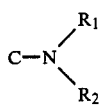

group;

$X_2$ represents N or the

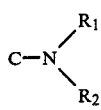

group provided that $X_1$ and $X_2$ are different from each other;

$R_1$ and $R_2$ represent $-(CH_2)_nOH$; $n=1$ to 4 or

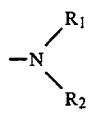

constitutes a saturated heterocycle with 5 or 6 groupings containing one nitrogen atom as heteroatom and bearing a substituent in 3 or 4 position selected from:

(i) a $-(CH_2)_mOR_6$ group where M is equal to 0, 1 or 2 and $R_6$ represents hydrogen or a

group or

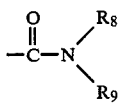

group in which $R_7$ represents a lower alkyl, a cycloalkyl group or a phenyl group possibly substituted by an atom of halogen and $R_8$ and $R_9$ considered independently each represent hydrogen or a lower alkyl;

(ii) an oxo (=O) group;

(iii) a spiro-1,3-dioxolane-2-yl

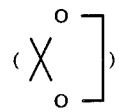

group;

Ar represents:

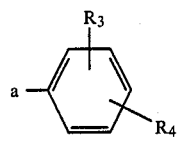

group in which $R_3$ designates hydrogen, an atom of halogen, a lower alkyl group, a lower alkoxy group, a trifluoromethyl group, a hydroxy group, a nitro group or a cyano group and $R_4$ designates hydrogen or an atom of halogen;

. a napththyl group non-substituted or monosubstituted by an atom of halogen;

$R_5$ designates hydrogen or an atom of halogen, it being understood that $R_5$ can be an atom of halogen only if $X_2$ represents an atom of nitrogen.

In the present invention, lower alkyl group is understood to mean a straight or branched alkyl group having from 1 to 5 atoms of carbon. Similarly, lower alkoxy group is understood to mean a lower -O-alkyl group.

More precisely, the compounds according to the invention are represented by one of the following two formulae:

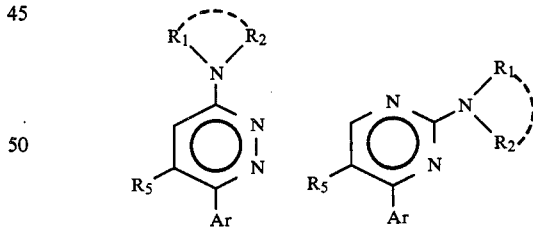

Ia    Ib

Compounds I yield salts with organic or inorganic acids. These salts, with the pharmaceutically acceptable acids, are an integral part of the invention.

Compounds I are prepared from the corresponding ketonic derivative obtained according to the methods described in the prior art. The ketonic derivative is converted into the corresponding chlorinated aromatic compound; then the latter is converted into corresponding aminated compound.

PREPARATION OF Ia

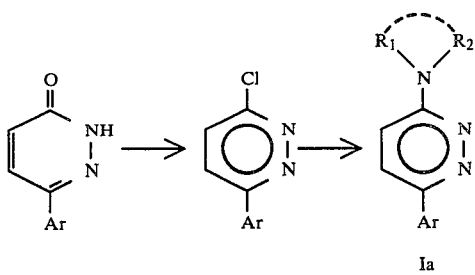

The 3-pyridazinones are prepared in accordance with the methods described in: Journal of the American Chemical Society, 1953, pp 1117–1119 and Journal of Organic Chemistry, 1973, 38, pp 4044–4048.

The 6-aryl-3-chloro-pyridazines are known compounds; they may be prepared for example according to the method described in: Journal of Heterocyclic Chemistry, 1973, 38, 881–892.

When one of the substituents $R_3$ or $R_4$ is hydroxyl, the latter must be blocked, for example by ethyl chloroformate, during preparation of the 6-aryl-3-chloro-pyridazine.

The substitution of the pyridazine by the hydroxylated amine group

is effected by heating 6-aryl-3-chloro-pyridazine and $HNR_1R_2$ amine in an alkanol at boiling temperature.

The product may then possibly be esterified by action of an acid chloride in the presence of a tertiary amine by heating the mixture in an aprotic solvent, for example tetrahydrofuran.

The N-monosubstituted carbamate may also possibly be prepared by addition on the hydroxylated amine of an isocyanate and heating in an aprotic solvent, for example tetrahydrofuran.

Similarly, the disubstituted N,N-carbamates are obtained by action of a carbamoyl chloride within a solvent such as dioxane at reflux and in the presence of a hydracid acceptor, such as triethylamine.

Finally, when the cyclic amine is substituted by an oxo group, compound I is obtained by acid hydrolysis of the corresponding cyclic acetal.

EXAMPLE 1

3-(4-hydroxy-piperidino)-6-(2-nitrophenyl)-pyridazine; SR41673

By using the methods described in the prior art, the 3-chloro-6-(2-nitro-phenyl)-pyridazine is prepared (m.p.: 138°–140° C.). 3 g of this product are mixed with 3.86 g of 4-hydroxy-piperidine in 60 ml of normal butanol and heated with stirring to 100° C. for 5 hours.

The reaction mixture is concentrated in vacuo to dryness, then the residue is taken up in water and extracted with ethyl acetate. The organic phase is washed with water, dried over sodium sulfate then concentrated to dryness. The residual oil is chromatographed over silica gel by using a chloroform/methanol (90/10 vol:vol) mixture as eluent. After evaporation of the solvents, the residual oil crystallizes. Recrystallization is carried out in acetonitrile to obtain 2.6 g of the expected product.

m.p. 138°–139° C.

EXAMPLE 2

3-(4-hydroxy-piperidino)-6-(2-chlorophenyl)pyridazine. CM 40907.

Operation is carried out in accordance with the methods mentioned for preparing 3-chloro-6-(2-chlorophenyl)pyridazine (m.p.: 146°–147° C.). 5 g of this product are dissolved in 120 ml of normal butanol and mixed with 6.74 g of 4-hydroxy-piperidine, then heated to reflux. By following the modus operandi described for the previous Example, 5 g of CM 40907 are obtained after recrystallization in absolute ethanol.

m.p.: 154°–155° C.

EXAMPLE 3

3-(4-butyroyloxypiperidino)-6-(2-chlorophenyl)-pyridazine; SR 41172

2.9 g of CM 40907 are dissolved in 100 ml of tetrahydrofuran, 3.5 ml of triethylamine and 2.6 g of butyryl chloride are added, then the mixture is heated to reflux for 3 days. 0.7 ml of triethylamine and 0.52 ml of butyryl chloride are added and the mixture is again heated to reflux for 24 hours. The reaction medium is then concentrated to dryness and the residue is taken up in normal hydrochloric acid and washed with ether.

After addition of sodium carbonate, the mixture is extracted with ethyl acetate. The organic phase is dried over sodium sulfate and concentrated to dryness. The residual oil is chromatographed over silica gel, using ethyl acetate as eluent. After concentration and recrystallization in isopropyl ether, 2.7 g of SR 41172 are obtained.

m.p. 89°–90° C.

EXAMPLE 4

3-(4-methylcarbamoyloxy-piperidino)-6-(2-chlorophenyl)pyridazine; SR 41820.

A solution of 2.7 g of CM 40907 in 50 ml of tetrahydrofuran is prepared. It is heated to reflux for 48 hours in the presence of 1.65 ml of methyl isocyanate; after having added 1.65 ml of ethyl isocyanate, heating is resumed for 48 hours.

The reaction medium is concentrated under vacuum, the residue is chromatographed over silica gel using ethyl acetate as eluent. After concentration, the product is recrystallized in ethyl acetate. 1 g of SR 41 820 is obtained.

m.p. 134°–136° C.

EXAMPLE 5

4-(dimethylcarbamoyl-4-oxy-piperidino)-6-(2,4-dichloro-phenyl)pyridazine; SR 42432.

(a)

3-(4-hydroxy-piperidino)-6-(2,4-dichloro-phenyl)-pyridazine; SR 41378

Operation is carried out as in Example 1 from 3-chloro-6-(2,4-dichloro-phenyl)pyridazine and 4-hydroxy-piperidine.

The expected product is obtained in the same way.

m.p. 151 3° C. (ethanol).

(b) SR 42432

4.7 g of the product obtained hereinabove are dissolved in 60 ml of dioxane then 6.3 ml of triethylamine and 4.1 ml of dimethylcarbamoyl chloride are added. The mixture is heated to reflux for 7 days then the solvent is evaporated to dryness under vacuum. The residue is taken up in an aqueous solution of 10% sodium carbonate and extracted with ethyl acetate. The organic layer is separated, dried over sodium sulfate and the solvent is evaporated to dryness in vacuo. The residue is chromatographed over silica gel, eluting with ethyl acetate. A product is obtained which crystallizes. After recrystallization in ethyl acetate, m.p. 197:198° C.; weight 2.8:g.

EXAMPLE 6

3-[1,4-dioxa-8-aza-spiro[4,5]decane-8-yl]-6-(2-chlorophenyl)pyridazine; SR 42487

The mixture of 4.5 g of 3-chloro-6-(2-chloro-phenyl)-pyridazine and 8.2 g of 1,4-dioxa-8-aza-spiro[4,5]decane in 100 ml of butanol is heated to reflux for 18 hours.

The butanol is evaporated to dryness in vacuo and the residue is taken up in water. The mixture is extracted with ethyl acetate and the organic solution is dried over sodium sulfate. The solvent is evaporated to dryness under vacuum and the residue is recrystallized in ethyl acetate, m.p.: 156°–158° C.; weight: 5.2 g.

EXAMPLE 7

3-(4-oxo-iperidino)-6-(2-chlorophenyl)pyridazine; SR. 42488

4 g of the product of Example 6 in the mixture of 40 ml of formic acid and 60 ml of water are heated to reflux for 4 hours. The reaction mixture is poured over a solution of sodium hydroxide in excess to which ice has been added. The mixture is extracted with methylene chloride, the organic layer is separated and dried over sodium sulfate.

The solvent is evaporated to dryness under vacuum then the residue is recrystallized in absolute ethanol. m.p.: 158°–160° C.; Weight: 3.2 g.

By using similar methods, the compounds according to the invention described in Table 1 hereinbelow are prepared.

TABLE I

| No. of Product | $-N\begin{smallmatrix}R_1\\R_2\end{smallmatrix}$ | Ar | m.p. °C. Solvent of crystallization |
| --- | --- | --- | --- |
| CM 40857 | —N(piperidine)—OH | phenyl-CF₃ | 130° C. ethyl acetate |
| CM 41096 | —N(piperidine with OH) | phenyl-Cl (2-) | 134° C. ethyl acetate |
| CM 41127 | —N(piperidine)—OH | phenyl-Cl (4-) | 174–176° C. absolute ethanol |
| SR 41155 | —N(piperidine)—OH | phenyl-Cl,Cl (2,3-) | 150–152° C. ethyl acetate |
| SR 41171 | —N(piperidine)—OH | phenyl | 150° C. (acetonitrile) |

TABLE I-continued

| No. of Product | —N(R1)(R2) | Ar | m.p. °C. Solvent of crystallization |
|---|---|---|---|
| SR 41173 | 4-(4-chlorobenzoyloxy)piperidin-1-yl | 2-chlorophenyl | 142–144° C. (acetonitrile) |
| SR 41174 | 4-(cyclopropanecarbonyloxy)piperidin-1-yl | 2-chlorophenyl | 88–90° C. methylene chloride-isopropyl ether |
| SR 41175 | 4-(pivaloyloxy)piperidin-1-yl | 2-chlorophenyl | 145° C. (acetonitrile) |
| SR 41184 | 4-hydroxypiperidin-1-yl | 4-fluorophenyl | 162–164° C. ethyl alcohol |
| SR 41185 | 4-hydroxypiperidin-1-yl | 4-methoxyphenyl | 182–184° C. ethyl alcohol |
| SR 41188 | 4-hydroxypiperidin-1-yl | 3-chlorophenyl | 152–154° C. ethyl acetate |
| SR 41254 | 3-hydroxypyrrolidin-1-yl | 2-chlorophenyl | 170–172° C. ethyl alcohol |
| SR 41259 | 3-(hydroxymethyl)pyrrolidin-1-yl | 2-chlorophenyl | 136–138° C. ethyl alcohol isopropyl ether |

TABLE I-continued

| No. of Product | —N⟨R₁/R₂ | Ar | m.p. °C. Solvent of crystallization |
|---|---|---|---|
| SR 41261 | piperidin-4-yl—CH₂CH₂OH | 2-Cl-phenyl | 88–90° C. (isopropanol-isopropyl ether) |
| SR 41558 | 4-hydroxypiperidin-1-yl | 2-F-phenyl | 132–134° C. (ethanol-isopropyl ether) |
| SR 41559 | 4-hydroxypiperidin-1-yl | 2-HO-phenyl | 141–143° C. (acetonitrile) |
| SR 41673 | 4-hydroxypiperidin-1-yl | 2-NO₂-phenyl | 138–139° C. (acetonitrile) |
| SR 41900 | 4-(OC(O)NHCH₃)piperidin-1-yl | 2,3-diCl-phenyl | 168–170° C. (acetonitrile) |
| SR 41915 | 4-(OC(O)NHCH₃)piperidin-1-yl | 4-Cl-phenyl | 216–218° C. (acetonitrile) |
| SR 41917 | 4-(OC(O)NHCH₃)piperidin-1-yl | 4-F-phenyl | 170–172° C. (acetonitrile) |
| SR 41930 | 4-hydroxypiperidin-1-yl | 4-OH-phenyl | 230° C. ethanol |
| SR 41931 | 4-hydroxypiperidin-1-yl | 3-NO₂-phenyl | 165° C. (acetonitrile) |

TABLE I-continued

| No. of Product | —N(R₁)(R₂) | Ar | m.p. °C. Solvent of crystallization |
|---|---|---|---|
| SR 41935 | piperidin-N-yl with 4-O-C(=O)-NHCH₃ | 3-Cl-phenyl | 164–166° C. ethyl acetate |
| SR 41965 | piperidin-N-yl with 4-O-C(=O)-NHCH₃ | 2-Cl-phenyl | 166–167° C. ethyl acetate |
| SR 41932 | 4-hydroxypiperidin-N-yl | 2,4-di-Cl-phenyl | 172–173° C. (ethanol) |
| SR 42087 | piperidin-N-yl with 4-O-CO-NH-(CH₂)₃-CH₃ | 4-Cl-phenyl | 156–158° C. ethyl acetate |
| SR 42093 | piperidin-N-yl with 4-O-CO-NH-C(CH₃)₃ | 2-Cl-phenyl | 154–155° C. ethyl acetate-isopropyl ether |
| SR 42095 | piperidin-N-yl with 4-O-CO-N(CH₃)₂ | 2-Cl-phenyl | 131° C. ethyl acetate-isopropyl ether |
| SR 42159 | 4-hydroxypiperidin-N-yl | 3-CN-phenyl | 136–138° C. ethyl acetate-isopropyl ether |
| SR 42356 | 4-hydroxypiperidin-N-yl | 3-CH₃-phenyl | 187–188° C. (methanol) |

TABLE I-continued

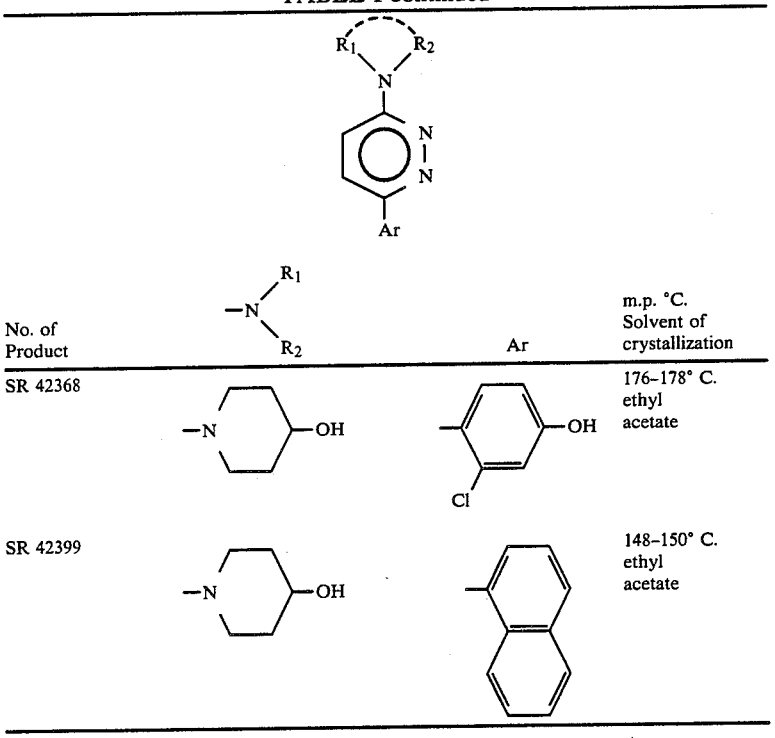

| No. of Product | −N⟨R₁R₂ | Ar | m.p. °C. Solvent of crystallization |
|---|---|---|---|
| SR 42368 | −N(piperidine)−OH | methyl-chloro-phenol-OH | 176–178° C. ethyl acetate |
| SR 42399 | −N(piperidine)−OH | methylnaphthyl | 148–150° C. ethyl acetate |

Preparation of 1b: Reaction scheme

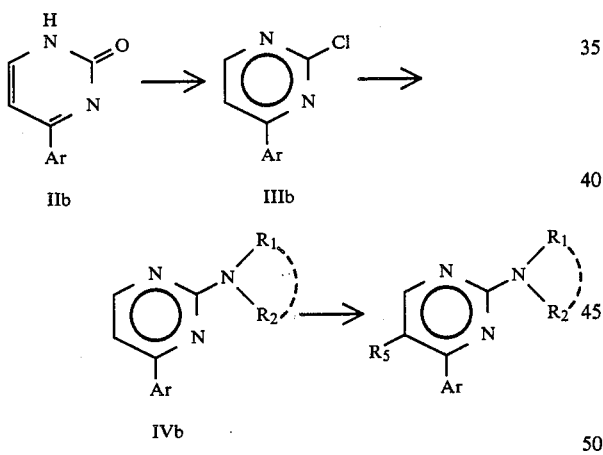

The 6-aryl-pyrimidine-2-ones (11b) are prepared in accordance with the method described in: Journal of Organic Chemistry, 1953, 18, pp 588–593.

Compounds III b and IV b are obtained by using the same methods as those used for the similar compounds in pyridazine series.

If R₅ is a halogen, halogenation of the pyrimidine nucleus for obtaining 1 b is effected by N-chloro-succinimide according to the method described in: Tetrahedron, 1966, 22, 2401.

EXAMPLE 8

2-(4-hydroxy-piperidino)-4-(2-chlorophenyl)pyrimidine; CM 40724.

(a) 4-(2-chloro-phenyl)-pyrimidine-2-one

The 2-chloro-benzoyl acetaldehyde is prepared according to the method described in: Berichte der Deutschen Chemischen Gesellschaft, 1901, 34, 3889–3897.

53.6 g of this product are dissolved in 2.5 l of absolute alcohol to which are added 17.63 g of urea and 29.35 ml of concentrated hydrochloric acid. After heating to reflux for one night, the reaction mixture is concentrated. The residue is taken up in diluted sodium hydroxide and extracted with ethyl acetate. The organic phase is washed with water, dried over sodium sulfate and concentrated to dryness.

The crystallized residue is chromatographed, then 10.1 g are dissolved in 500 ml of ethanol. 4.54 g of potassium hydroxide dissolved in 50 ml of water are added, then the mixture is heated to reflux for 30 minutes. After having concentrated the reaction mixture under vacuum, the residue is neutralized by dilute hydrochloric acid.

The organic phase is extracted with methylene chloride, washed with water, dried over sodium sulfate then concentrated. The crystallized residue is washed with 50 ml of ethyl acetate to yield 6 g of white product.

m.p.: 210°–212° C.

(b) 2-chloro-4-(2-chloro-phenyl)pyrimidine

This product is obtained by action of phosphorus oxychloride hot according to the method mentioned for the preparation of 1 a.

m.p.: 100° C. (hexane)

(c) CM 40724

The modus operandi described in Example 1 is used for adding 4-hydroxy-piperidine.

m.p.: 102°–104° C. (isopropyl ether).

EXAMPLE 9

Hydrobromide of 5-chloro-6-(2-chlorophenyl)-2-(4-hydroxy-piperidino)-pyrimidine; SR 40858

2.7 g of CM 40724 are dissolved in 50 ml of chloroform. 1.37 g of N-chloro-succinimide are added and the reaction mixture is heated to reflux for one night, then concentrated under vacuum. The residue is taken up in 50 ml of boiling water, the slightly cooled mixture is extracted with ethyl acetate. The organic phase is decanted, dried over sodium sulfate then concentrated. The residual oil is chromatographed over silica gel using as eluent a cyclohexane-ethyl acetate (50/50 vol:-vol) mixture. After elimination of impurities at the head of the column, the product described is eluted. The concentration of the fractions yields 1.9 g of oil which is taken up in 100 ml of ether.

After bubbling hydrobromic gas up to acid pH, the hydrobromide of the product crystallizes. It is recrystalized in acetonitrile.

m.p. 192.194° C.

By following the methods of preparation indicated, the compounds according to the invention described in Table II hereinbelow are obtained.

TABLE II

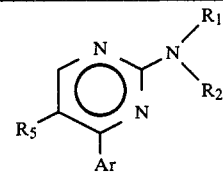

| No. of product | $R_1$, $R_2$ (as $-N<^{R_1}_{R_2}$) | $R_5$ | Ar | m.p. °C. solvent of crystallization |
|---|---|---|---|---|
| SR 41554 | $-N\underset{\diagdown}{\diagup}\!\!-\!\!OH$ (piperidine-OH) | H | -C$_6$H$_4$-Cl | 140–142° C. isopropyl ether |
| SR 41556 | $-N\underset{\diagdown}{\diagup}\!\!-\!\!OH$ (piperidine-OH) | Cl | -C$_6$H$_4$-Cl | 144° C. isopropyl ether |
| SR 41590 | $-N(CH_2-CH_2-OH)_2$ | H | -C$_6$H$_4$-Cl | 114° C. isopropyl ether |
| SR 41591 | $-N(CH_2-CH_2-OH)_2$ | H | -C$_6$H$_4$-Cl (2-Cl) | 106–108° C. isopropyl ether |

The products according to the invention have been assessed for their hypnogenic and sedative effects, as well as for their anti-epileptic activity.

I-ASSESSMENT OF THE HYPNOGENIC AND SEDATIVE EFFECT OF THE PRODUCTS a. Effect of the products on the spontaneous motility.

The sedative effect is translated by the reduction of the spontaneous motility of the animals. This was measured by the actimeter test developed by BOISSIER and SIMON (1965). The equipment was composed of actimetric cages, of the Apelab type (26×21.5×10 cm), through which pass two light rays which act on a photoelectric cell. The batches were constituted by 12 female Charles River CD1 mice weighing between 20 and 24 g. The animals were placed individually in the cages 45 minutes after the oral administration of the products at the dose of 250 mg/kg or at the dose of 100 mg/kg. Each passage through a light beam was counted by an individual meter. The scores corresponding to the movements of the animals were recorded for 10 minutes and compared with the scores made by the batches of control animals, treated solely by the vehicle (0.1N HCl).

Comments

After administration, at the oral dose of 100 mg/kg or of 250 mg/kg, the products of the invention reveal a powerful sedative effect characterized by a considerable reduction in the motility of the animals.

On the other hand, at the dose of 100 mg/kg, the CM 41378 provokes a loss of turnaround reflex characteristic of a sleep-inducing effect in 50% of the animals treated.

TABLE III

| Products | Dose p.o. mg/kg | Locomotor activity Score (p.cent/controls) |
|---|---|---|
| CM 40857 | 100 | −87%** |
| CM 40907 | 100 | −66%** |
| CM 41127 | 100 | −68%** |
| SR 41155 | 100 | −82%** |
| SR 41171 | 100 | −34% |
| SR 41172 | 100 | −32%** |
| SR 41184 | 100 | −91%** |
| SR 41188 | 100 | −77%** |
| SR 41254 | 100 | −34%* |
| SR 41259 | 100 | −19% |
| SR 41261 | 100 | −27%* |
| CM 40858 | 250 | −20% |
| SR 41185 | 250 | −78%** |
| SR 41554 | 250 | −26%* |
| SR 41556 | 250 | −29%** |
| SR 41558 | 250 | −93%** |
| SR 41559 | 250 | −66%** |
| SR 41654 | 250 | −57%** |
| SR 41673 | 250 | −61%** |
| SR 41174 | 100 | −15% |
| SR 41932 | 150 | −59%** |
| SR 42095 | 10 | −28* |
| SR 42487 | 100 | −42%** |

*p 0,05 (Student test)
**p 0,01 (Student test)

b. Potentialization of narcosis by pentobarbital

With a view to assessing the hypnogenic power of the products, we have studied their capacity to potentialize the effects of a subnarcotic dose of pentobarbital in the mouse. The batches were constituted by 10 Charles River CD1 mice, weighing between 20 and 24 g. The pentobarbital (20 mg/kg, i.p.) was administered 60 minutes after administration of the products. The criterion of sleep-induction retained was the loss of the turnaround reflex. The animals which did not present this reflex were counted.

| Products | Potentialization of pentobarbital ED$_{50}$ (mg/kg, p.o.) |
|---|---|
| CM 40907 | 96 |

-continued

| Products | Potentialization of pentobarbital ED$_{50}$ (mg/kg, p.o.) |
|---|---|
| SR 41155 | 20 |
| SR 41378 | 21 |
| SR 41554 | 66 |
| SR 42095 | 7,4 |
| SR 42488 | 67 |

The products according to the invention are capable of potentializing narcosis by pentobarbital; this property is predictive of a hypnogenic effect.

II-ASSESSMENT OF THE ANTI-EPILEPTIC ACTIVITY OF THE PRODUCTS

The anti-epileptic effect of the products in the mouse was assessed on a model of convulsions provoked by an electric shock, and on a model of convulsions induced by a chemical agent: bicuculline.

a. Antagonism of the convulsions induced by an electric shock

The test was slightly modified from that of SWINYARD et al (1952) and ASAMI et al (1974). The equipment was composed of a Racia shock generator provided with two ocular electrodes delivering a current of 12.5 volts for 0.3 seconds. The batches were constituted by 10 Charles River CD1 mice, weighing between 20 and 24 g. The products were administered by the oral route, 60 minutes before the electric shock. The animals presenting no tonic extension of the rear limbs were considered as being protected from the convulsive crisis.

b. Antagonism of the convulsions provoked by bicuculline

The batches were constituted by 10 Charles River CD1 mice, weighing between 20 and 22 g. The products were administered by the oral route, 60 minutes before the bicuculline (0.8 mg/kg, i.v.). The appearance of tonic convulsions was noted during the 60 minutes following the injection of the bicuculline.

Comments

After oral administration in the mouse, the products according to the invention show antiepileptic properties both with respect to electric shock and bicuculline.

TABLE IV

| | Median effective dose (ED$_{50}$) (mg/kg, p.o.) | |
|---|---|---|
| Products | Antagonism of the electric shock | Antagonism of Bicuculline |
| CM 40857 | 63 | |
| CM 40858 | 49 | |
| CM 40907 | 16 | 38 |
| CM 41127 | 28 | 98 |
| SR 41171 | 86 | 83 |
| SR 41172 | 28 | 39 |
| SR 41184 | 48 | |
| SR 41188 | 45 | |
| SR 41378 | 30 | 5,7 |
| SR 41554 | 145 | 147 |
| SR 41558 | 115 | 30 |
| SR 41673 | 27 | 81 |
| SR 41820 | 10 | 13 |
| SR 41174 | 92 | |
| SR 41932 | 30 | 131 |
| SR 42095 | 2 | 1,6 |
| SR 42399 | 38 | |

TABLE IV-continued

| | Median effective dose (ED$_{50}$) (mg/kg, p.o.) | |
|---|---|---|
| Products | Antagonism of the electric shock | Antagonism of Bicuculline |
| SR 42487 | 57 | |
| SR 42488 | 40 | 35 |

III-DETERMINATION OF THE LETHAL DOSE IN THE MOUSE AFTER ACUTE ADMINISTRATION OF THE PRODUCTS

The products were administered by the oral route to batches of 5 female Charles River CD1 mice, weighing between 20 and 24 g. They were solubilized in 0.1N HCl.

Toxicity was noted during the 72 hours following administration of the products. The LD$_{50}$ was calculated for two products.

TABLE V

| | % of toxicity or LD$_{50}$ | | |
|---|---|---|---|
| Products | 250 mg/kg p.o. | 500 mg/kg p.o. | 1000 mg/kg p.o. |
| CM 40858 | 0 | 0 | 0 |
| CM 40907 | | DL$_{50}$ = 807 | |
| CM 41127 | 0 | 0 | |
| SR 41155 | 0 | 100 | 100 |
| SR 41171 | 0 | 0 | 100 |
| SR 41172 | 0 | 0 | 100 |
| SR 41184 | 0 | 60 | 100 |
| SR 41185 | 0 | 0 | 0 |
| SR 41188 | 0 | 0 | 60 |
| SR 41254 | 0 | 0 | 20 |
| SR 41378 | | DL$_{50}$ = 423 | |
| SR 41554 | 0 | 0 | 0 |
| SR 41556 | 0 | 0 | 0 |
| SR 41558 | 0 | 0 | 80 |
| SR 41559 | 0 | 0 | 0 |
| SR 41590 | 0 | 0 | 40 |
| SR 41591 | 0 | 0 | 0 |
| SR 41654 | 0 | 0 | 60 |
| SR 41673 | 0 | 0 | 20 |
| SR 41932 | 0 | 0 | 100 |
| SR 42094 | 0 | 0 | 0 |
| SR 42399 | 0 | 0 | |
| SR 42487 | 0 | 0 | 0 |
| SR 42488 | 0 | 0 | 0 |

The results expressed in percentage of animals which die in the 71 hours consecutive to the oral administration of the products are noted in the preceding Table.

The tests thus effected show that the products according to the invention present interesting pharmacological properties and a low toxicity. They may be used in human therapeutics, particularly for the treatment of psychic, neurological or neuromuscular disorders.

The products according to the invention may be used in particular for the treatment of disorders in mood or in the behaviour: nervosity, irritability as well as for the treatment of anxious states, insomnias and epilepsy.

These products may be administered by the oral route or by the injectable route. The pharmaceutical compositions may be solid or liquid and may be in the form for example of tablets, capsules, granules, suppositories or injectable preparations.

Posology may vary in large proportions, in particular, depending on the type and seriousness of the disorder to be treated and depending on the mode of administration. In the adult by the oral route, it is most often included between 1 mg and 500 mg per day, possibly spread out in several doses.

By way of example, the following Galenic preparation may be indicated:

Capsules

| | |
|---|---|
| CM 40907 | 100 mg |
| Aerosil | 0.5 mg |
| Magnesium stearate | 1.5 mg |
| Starch STA RX 1500 | 48 mg |
| | 150 mg |

What is claimed is:

1. Heterocyclic compounds of formula:

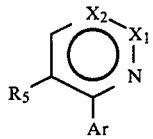

in which:

$X_1$ represents N or the group

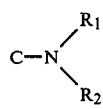

$X_2$ represents N or the group

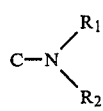

on condition that $X_1$ and $X_2$ are different from each other;

$R_1$ and $R_2$ represent —$(CH_2)_nOH$; n=1 to 4 or

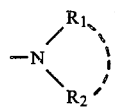

constitutes a saturated heterocycle with 5 or 6 groupings having one nitrogen atom as heteroatom and being substituted in 3 or 4 position by a group selected from:

(i) a —$(CH_2)_mOR_6$ group where m is equal to 0, 1 or 2 and $R_6$ represents hydrogen or a group

or

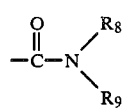

in which $R_7$ represents a lower alkyl, a cycloalkyl group or a phenyl group optionally substituted by an atom of halogen and $R_8$ and $R_9$ considered independently each represent hydrogen or a lower alkyl;

(ii) an oxo (=O) group;

(iii) a spiro-1,3-dioxolane-2-yl group;

Ar represents:

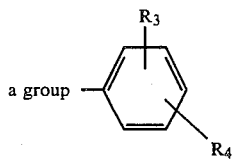

in which $R_3$ designates hydrogen, an atom of halogen, a lower alkyl group, a lower alkoxy group, a trifluoromethyl group, a hydroxy group, a nitro group or a cyano group, and $R_4$ designates hydrogen or an atom of halogen;

a naphthyl group non-substituted or monosubstituted by an atom of halogen;

$R_5$ designates hydrogen or an atom of halogen, it being understood that $R_5$ is an atom of halogen only if $X_2$ represents an atom of nitrogen;

and the salts of said compounds with pharmaceutically acceptable acids.

2. The compounds of claim 1, wherein they correspond to formula:

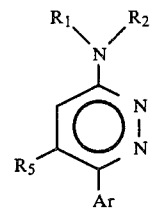

in which Ar, $R_1$, $R_2$ and $R_5$ are as defined in claim 1.

3. The compounds of claim 1, wherein they correspond to formula:

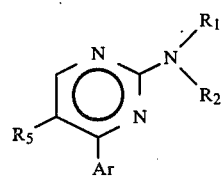

in which Ar, $R_1$, $R_2$ and $R_5$ are as defined in claim 1.

4. Heterocyclic compounds of claim 1, wherein $R_5$ is H $X_1$ is N $X_2$ is

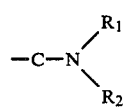

wherein

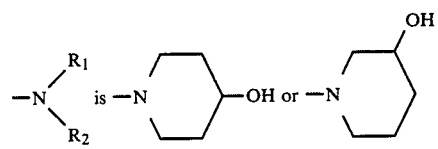 is 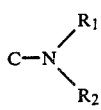

Ar is a phenyl group, a phenyl group mono-substituted by a chloro, a fluoro, a methyl, a methoxy, a nitro, a hydroxy, a cyano, a trifluoromethyl group, or a phenyl group disubstituted by two chloro groups or by a hydroxy and a chloro group or Ar is a naphthalene group.

5. Heterocyclic compounds of claim 1, wherein
$X_1$ is N
$X_2$ is

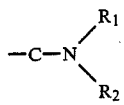

wherein

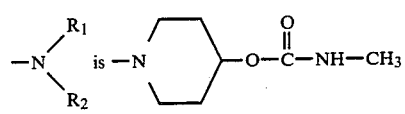

$R_5$ is H
Ar is a phenyl group mono-substituted by a chloro or a fluoro group or a dichloro-phenyl group.

6. Heterocyclic compounds of claim 1, wherein
$X_1$ is N
$R_5$ is H
$X_2$ is

wherein

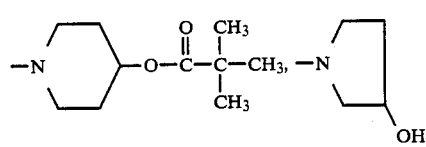

is selected from the groups consisting of

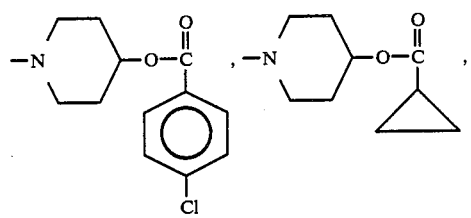

-continued and Ar is a chlorophenyl group.

7. Heterocyclic compounds of claim 1, wherein
$X_1$ is N;
$R_5$ is H;
$X_2$ is

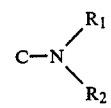

wherein

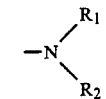

is selected from the groups consisting of

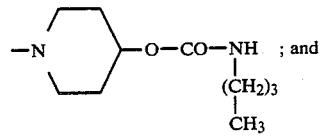

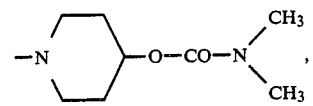

and Ar is a chlorophenyl group.

8. Heterocyclic compounds of claim 1, wherein
—$X_2$ is N
—$X_1$ is

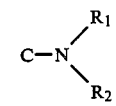

wherein

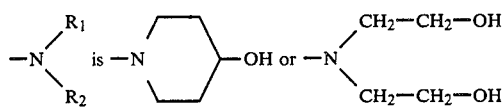

$R_5$ is H or Cl and

Ar is a chlorophenyl group.

9. A heterocyclic compound of claim 1, which is 3-(4-hydroxy-piperidino)-6-(2-chloro-phenyl)pyridazine.

10. A heterocyclic compound of claim 1, which is 3-(4-hydroxy-piperidino)-6-(2,4-dichloro-phenyl)-pyridazine.

11. Pharmaceutical compositions active on the central nervous system, wherein they contain a therapeutically effective amount of at least one compound according to claim 1.

12. The pharmaceutical compositions of claim 11, wherein they are administered by the oral route and comprise per unit dose from 1 to 500 mg of active product.

13. The pharmaceutical compositions of claim 11, wherein they are in a form appropriate for administration by the injectable route.

14. A method of treating central nervous system disorders, comprising administering to a patient in need of such treatment an effective amount of a compound defined in claim 1.

15. A method of treating a patient in need of a sedative or anticonvulsant effect, comprising administering an effective amount of a compound defined in claim 2.

16. A method of treating a patient in need of a sedative or anticonvulsant effect, comprising administering an effective amount of a compound defined in claim 3.

17. A method of treating a patient in need of a sedative or anticonvulsant effect, comprising administering an effective amount of a compound defined in claim 4.

18. A method of treating a patient in need of a sedative or anticonvulsant effect, comprising administering an effective amount of a compound defined in claim 5.

19. A method of treating a patient in need of a sedative or anticonvulsant effect, comprising administering an effective amount of a compound defined in claim 6.

20. A method of treating a patient in need of a sedative or anticonvulsant effect, comprising administering an effective amount of a compound defined in claim 7.

21. A method of treating a patient in need of a sedative or anticonvulsant effect, comprising administering an effective amount of a compound defined in claim 8.

22. A method of treating a patient in need of a sedative or anticonvulsant effect, comprising administering an effective amount of a compound defined in claim 9.

23. A method of treating a patient in need of a sedative or anticonvulsant effect, comprising administering an effective amount of a compound defined in claim 10.

* * * * *